(12) United States Patent
Shetty

(10) Patent No.: US 10,391,138 B2
(45) Date of Patent: Aug. 27, 2019

(54) MULTIDIMENSIONAL APPROACH FOR CANCER TREATMENT

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 0 days.

(21) Appl. No.: 16/031,820

(22) Filed: Jul. 10, 2018

(65) Prior Publication Data

US 2018/0318376 A1    Nov. 8, 2018

Related U.S. Application Data

(60) Provisional application No. 62/531,205, filed on Jul. 11, 2017.

(51) Int. Cl.
| | | |
|---|---|---|
| *A61K 36/81* | (2006.01) | |
| *A61K 33/10* | (2006.01) | |
| *A61K 33/26* | (2006.01) | |
| *A61K 33/30* | (2006.01) | |
| *A61K 33/34* | (2006.01) | |
| *A61K 36/53* | (2006.01) | |
| *A61K 36/59* | (2006.01) | |
| *A61K 36/67* | (2006.01) | |
| *A61K 36/68* | (2006.01) | |
| *A61K 36/8965* | (2006.01) | |
| *A61K 36/9066* | (2006.01) | |
| *A61K 36/9068* | (2006.01) | |
| *A61P 35/02* | (2006.01) | |
| *A61K 45/06* | (2006.01) | |

(52) U.S. Cl.
CPC .............. *A61K 36/81* (2013.01); *A61K 33/10* (2013.01); *A61K 33/26* (2013.01); *A61K 33/30* (2013.01); *A61K 33/34* (2013.01); *A61K 36/53* (2013.01); *A61K 36/59* (2013.01); *A61K 36/67* (2013.01); *A61K 36/68* (2013.01); *A61K 36/8965* (2013.01); *A61K 36/9066* (2013.01); *A61K 36/9068* (2013.01); *A61P 35/02* (2018.01); *A61K 45/06* (2013.01); *A61K 2300/00* (2013.01)

(58) Field of Classification Search
CPC ........ A61K 36/81; A61K 36/59; A61K 36/68; A61K 36/53; A61K 36/9066; A61K 36/67; A61K 36/9068; A61K 33/34; A61K 33/30; A61K 33/26; A61K 33/10; A61K 36/8965; A61K 45/06; A61K 2300/00; A61P 35/02
See application file for complete search history.

(56) References Cited

U.S. PATENT DOCUMENTS

| | | | | |
|---|---|---|---|---|
| 6,080,401 | A * | 6/2000 | Reddy ................. | A61K 36/235 424/725 |
| 2003/0152585 | A1* | 8/2003 | Solanki ................. | A61K 36/21 424/195.15 |
| 2004/0009240 | A1* | 1/2004 | Solanki ............... | A61K 36/185 424/725 |
| 2007/0122494 | A1* | 5/2007 | Managoli ............. | A61K 36/185 424/725 |
| 2010/0093870 | A1* | 4/2010 | Ray ........................ | A61K 31/12 514/690 |

FOREIGN PATENT DOCUMENTS

EP    2090315 A1 *  8/2009  ............. A61K 36/00

OTHER PUBLICATIONS

Verma et al. International Journal of Green Pharmacy, 2015, 9(4): S20-S23. (Year: 2015).*
Remya et al. International Ayurvedic Medical Journal, Jan. 2017, 5(1): 79-89. (Year: 2017).*
Bendale et al. Rasamruta, 2015, 7(115): 1-5. (Year: 2015).*
Ahmed et al. Evid Based Complement Alternat Med., 2013, pp. 1-13. (Year: 2013).*
Sunnantran et al. Evidenced-Based Complementary and Alternative Medicine, 2012, pp. 1-11. (Year: 2012).*
Pal, Sanjoy. International Journal of Interdisciplinary and Multidisciplinary Studies (IJIMS), 2014, 1(6): 1-11. (Year: 2014).*
Pal, Sanjoy. Recent Patents on Nanomedicine, 2015, 5: 12-18. (Year: 2015).*
Kapoor, RC. Indian Journal of Traditional Knowledge, 2010, 9(3): 562-575. (Year: 2010).*
Dhruva et al. The Journal of Alternative and Complementary Medicine, 2014, 20(5): 364-370. (Year: 2014).*

* cited by examiner

*Primary Examiner* — Doan T Phan
(74) *Attorney, Agent, or Firm* — Pilloff & Passino LLP; Sean A. Passino; Rachel K. Pilloff

(57) ABSTRACT

Method of treating/managing Cancer is disclosed in various embodiments herein. The disclosed method includes the use of a combination of formulations and therapies that provide a holistic approach in treating or managing cancer. The method further includes practices of Ayurveda that facilitate in holistic healing of cancer patients.

16 Claims, No Drawings

MULTIDIMENSIONAL APPROACH FOR CANCER TREATMENT

CROSS REFERENCE TO RELATED APPLICATION

This application is based on and derives the benefit of U.S. Provisional Application 62/531,205 filed on Jul. 11, 2017, the contents of which are incorporated herein by reference.

TECHNICAL FIELD

The embodiments disclosed in this specification relates to a method for the treatment and management of Cancer rand more particularly to the use of Ayurveda in treating/managing abnormal cell proliferation or cancer

BACKGROUND

Cell proliferation is a highly regulated activity. Most cells are in a non-proliferative state unless they are stimulated. The loss of proliferative control leads to undesired abnormal cell proliferation and accumulation. Such accumulation of abnormal cells, commonly referred to as tumor, is a main characteristic of Cancer. Cancer can be of various types such as sarcoma, lymphoma, leukemia, melanoma, etc., depending on the type of cell that may be affected.

Cancer is one of the most dreaded diseases. It is considered to be one of the most leading causes of death worldwide. For years, pharmaceutical industries and research institutes have been making best efforts in finding an effective treatment for cancer.

Modern medicine offers various methods of treating cancer, which includes chemotherapy, radiation therapy, hormone therapy, targeted therapy etc. The type of treatment opted depends on location and stage of cancer. Although, evolutionary changes have occurred over the years in finding a treatment for cancer, these methods have been observed to have drawbacks. These commonly used treatment methods tend to affect healthy tissue, in addition to cancer tissues, thereby resulting in side effects such as Alopecia, Lymphedema, Pain, Bleeding, Bruising, Edema, Skin and Nail changes, Fertility problems, etc. These side effects in turn have adverse effects on patients, at a physical, mental, emotional and social level.

In modern science, disease is considered as an enemy, hence all the treatment regime is focused on the disease alone. However, in Ayurveda, the treatment regime is targeted not just towards the disease but also towards ensuring physical and mental well being of the body. This provides additional support for eradicating the disease. When a patient is mentally and physically prepared for this holistic approach, it becomes much easier for him/her to tolerate a dreaded condition like cancer. It is believed that if in one's life if he/she cultivates "appreciative joy" his health improves remarkedly.

Many ayurvedic treatment methods have also been used to treat cancer. With the knowledge of the anti-tumor properties of herbs such as *Silybum marianum, Aloe barbadensis, Curcuma longa, Zingiber officinale, Hydrastis canadensis, Annona muricata*, etc, numerous herbal formulations including such herbs have been developed. Various treatment regimens have also been developed and are used by Ayurveda practitioners in an attempt to treat cancer. However, there still exists a need for an effective method of treating abnormal cell proliferation leading to cancer.

OBJECTS OF THE DISCLOSED EMBODIMENTS

The principal object of the embodiments disclosed herein is to provide a method of treating Cancer.

A second object of the embodiments disclosed herein is to provide a method of managing abnormal cell proliferation.

Yet, another object of the embodiments disclosed herein is to provide the use of herbo-mineral formulation in treating and managing Cancer.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a method for the treatment and management of cancer. The method disclosed in the various embodiments herein is a holistic approach to achieve healing of patients having cancer or abnormal cell growth. In an embodiment the method is a holistic approach in cancer management.

Method

Disclosed herein are embodiments of a method of treating/managing cancer. The embodiments disclosed herein are also instrumental in treating/managing abnormal cell proliferation.

In an embodiment, the method includes administering to a patient a therapeutically effective amount of a herbo-mineral formulation and a bioactive formulation. In another embodiment, the method further comprises of administering to a patient a therapeutically effective amount of a target specific formulation.

In another embodiment, the method may further additionally comprise of atleast one of applying detoxification therapies; maintaining a specific diet; maintaining a healthy lifestyle; meditating; and applying pyramid therapy.

In an embodiment, the patient may be any individual in need of such treatment including ones having/expected or suspected of having cancer, tumor, cancer associated complications etc. Further, the patient may also be any individual having a condition involving abnormal, unregulated cell proliferation of any cell type including conditions such as carcinoma of oesophagus, carcinoma of lung, bronchogenic carcinoma, adenocarcinoma of endometrium, adenocarcinoma of rectum, Non-Hodgkin's lymphoma, Dalton Cell lymphoma, chronic myeloid leukemia, borderline mucinous tumor, adenocarcinoma of colon, fibro sarcoma, ovarian carcinoma, Cervix Adenocarcinoma, carcinoma of pancreas etc. Experimental studies show significant improvement in cases of Dalton Cell lymphoma. In a specific embodiment, the patient includes an individual having Dalton Cell lymphoma. The patient may further include individuals having undergone prior cancer treatment procedures such as chemotherapy, radiation therapy, surgery, or no prior cancer treatment procedures. In another embodiment, the cancer cells include any cells that are cancerous in nature including Human Cervix Adenocarcinoma cells, Human Lung Carcinoma cells, Human Ovarian Cancer cells etc.

In the embodiments disclosed herein, the term "therapeutically effective amount" includes any amount effective in treating a disease or disorder disclosed herein, such as cancer.

Herbo-mineral Formulation

The herbo-mineral formulation instrumental in the method disclosed in the various embodiments herein include a combination of selected herbs and minerals. In an embodiment, the herbo-mineral formulation includes *Withania somnifera* (6 to 10 wt %), *Sida cordifolia* (6 to 10 wt %), *Asparagus racemosus* (4 to 8 wt %), *Tinospora cordifolia* (4 to 8 wt %), *Moringa oleifera* (4 to 8 wt %), *Picrorhiza kurroa* (4 to 8 wt %), *Ocimum* sanctum (4 to 8 wt %), *Curcuma longa* (5 to 9 wt %), shilajit (4 to 8 wt %), Abhraka Bhasma (2 to 4 wt %), Trivanga Bhasma (0 to 2 wt %), Pravala Bhasma (0 to 2 wt %), Loha Bhasma (2 to 4 wt %) and Swarna Makshika Bhasma (0 to 2 wt %). In an embodiment, the herbo-mineral formulation may further include atleast one herb selected from a group consisting of *Terminalia chebula*, *Terminalia bellerica*, *Emblica officinalis*, *Piper longum*, *Piper nigrum* and *Zingiber officinalis*. In another embodiment, the herbo-mineral formulation may include herbs and minerals as depicted in Table 1.

The herbo-mineral formulation may be administered in any dosage form suitable for oral administration. The herbo-mineral formulation is preferably administered in the form of 500 mg tablets. For example: Table 1 depicts an embodiment of the herbo-mineral formulation in 500 mg tablet form.

Bioactive Formulation

The bioactive formulation disclosed in the various embodiments herein may include any formulation known for enhancing immunity or having Immuno-stimulating/Immuno-modulating properties. In an embodiment, the bioactive formulation is one having nano-organo-metallic complexes obtained by processing gold nano-particles with herbs. In another embodiment, thebioactive formulation includes Swarna bhasma. Such bioactive formulation may be any formulation having Swarna bhasma and/or other Immunostimulants/Immunomodulators. In another embodiment, the bioactive formulation includes processed swam abhasma and medicated honey.

Swarna Bhasma

In an embodiment, the swarna bhasma is processed swarna bhasma. In an embodiment, the processed swarna bhasma is prepared by triturating swarna bhasma in herb extracts. In another embodiment, the herb extracts may include extracts of the herbs *Saussurea lappa, Acorus calamus, Convolvulus pluicaulis, Tylophora indica, Murraya kinigi, Cynadon dactylon, Glycerrhiza glabra, Tinospora cordifolia* and *Centella asiatica*. The herbs disclosed herein, may be included in the formulation in any form that is generally known in the field. For example, the herbs may be used in form of extracts, concentrates, pellets, powder or other dried forms, etc. In an embodiment, the herbs are used in the form of fresh juice and/or decoctions which is further incorporated into the formulation. Table 1(a) lists the herbs and the preferable form of the extract.

TABLE 1(a)

List of herbs.

| No. | Botanical name | Sanskrit name | Form |
|---|---|---|---|
| 1 | *Saussurea lappa* | Kushtha | Decoction |
| 2 | *Acorus calamus* | Vacha | Decoction |
| 3 | *Convolvulus pluicaulis* | Shankhapushpi | Fresh juice |
| 4 | *Tylophora indica* | Arkapushpi | Fresh juice |
| 5 | *Murraya kinigi* | Kaidarya | Fresh juice |
| 6 | *Cynadon dactylon* | ShvetaDurva | Fresh juice |
| 7 | *Glycerrhiz aglabra* | Yashtimadhu | Decoction |
| 8 | *Tinospora cordifolia* | Guduchi | Fresh juice |
| 9 | *Centella asiatica* | Mandookaparni | Fresh juice |

TABLE 1

| Sl. No | Sanskrit Name | Part used | Latin/English name | Quantity |
|---|---|---|---|---|
| 1. | Ashvagandha | Dried root | *Withania somnifera* | 40 mg |
| 2. | Bala | Dried root | *Sida cordifolia* | 40 mg |
| 3. | Hareetakee | dry fruits | *Terminalia chebula* | 20 mg |
| 4. | Vibhitaki | dried fruits | *Terminalia bellerica* | 20 mg |
| 5. | Amalaki | dried fruits | *Emblica officinalis* | 20 mg |
| 6. | Shilajatu | Fossil resin | *Asphaltum punjabianum* | 30 mg |
| 7. | Shatavari | Dried root | *Asparagus racemosus* | 30 mg |
| 8. | Guduchi | Dried stem | *Tinospora cordifolia* | 30 mg |
| 9. | Pippali | Dried fruit | *Piper longum* | 20 mg |
| 10. | Maricha | Dried fruit | *Piper nigrum* | 20 mg |
| 11. | Shunthi | Dried rhizome | *Zingiber officinalis* | 20 mg |
| 12. | Shigru | Dried stem bark | *Moringa oleifera* | 30 mg |
| 13. | Katuki | Dried root | *Picrorhiza kurroa* | 30 mg |
| 14. | Tulasi | Dried leaves | *Ocimum sanctum* | 30 mg |
| 15. | Haridra | Dried rhizome | *Curcuma longa* | 35 mg |
| 16. | Trivanga Bhasma | Incinerated tin, lead and zinc | Stanni-plumbi et Zinc oxidum | 5 mg |
| 17. | Swarna Makshika bhasma | Incinerated copper pyrite | Oxidum copper pyrite | 5 mg |
| 18. | AbhrakaBhasma | Incinerated mica | Mica oxidum | 10 mg |
| 19. | Loha bhasma | Mineral | Incinerated Iron(ferric oxide) | 10 mg |
| 20. | Pravala bhasma | Mineral | Coral calx (calcium carbonate) | 5 mg |
| 21. | Excipient | Gum | Gum acacia | 50 g |

Honey

In an embodiment, the medicated honey is specifically cultured honey. In an embodiment, the specifically cultured honey is achieved by bee keeping in gardens having selected medicinal plants with flowers possessing anticancer, anti-oxidant, antimicrobial and anti-inflammatory properties. Anticancer flowers such as *Jaminum officinale, Plumeria rubra, Vinca rosea, Abelmoschus esculentus, Bauhinia tomentosa, Cucumis sativus, Butea monosperma, Toddalia asiatica, Annona squamosa*, etc are cultivated in the garden so that nectar procured by the honey bees possesses added anticancer value. The honey thus formed may then be harvested by methods known in the field.

Target Specific Formulation

The target specific formulation disclosed in the various embodiments herein may include any formulation known for treating cancer. In an embodiment, the target specific formulation may be selected to specifically target a particular type of cancer. The target specific formulation may be selected based on the type, site, stage of cancer, presenting symptoms, associated symptoms and other health problems etc. For example, use of hepatoprotective and liver stimulant tablets for patients having hepatocellular carcinoma, use of brain stimulant tablet for brain tumors, use of lung protective tablet and syrup for Lung cancer, use of uterine sedative and tonic tablet/syrup for uterine cancer, use of gum protective tablets and oil for oral cancer, etc.

In an embodiment, the target specific formulation may be any allopathic formulations known to treat cancer. In an embodiment, the target specific formulation may include atleast one of generally known chemotherapeutic agents such as purine ring inhibitors, ribonucleotide reductase inhibitors, dTMP synthesis inhibitors, DNA synthesis inhibitors, DNA intercalators, protein synthesis inhibitors, microtubule function inhibitors, etc.

In another embodiment, the target specific formulation may be any herbal formulation known to treat cancer. The herbal formulations may be any herbal formulation having herbs with anti-cancer properties. The list of herbs include herbs such as *Withania somnifera, Sida cordifolia, Bauhinia variegate, Piper longum, Piper nigrum, Zingiber officinalis, Moringa oleifera, Semecarpus anacardium, Ocimum sanctum, Emblica officinalis, Murraya koenigii*, etc. In an embodiment, the target specific formulation may include atleast one herbal formulations generally known to treat cancer such as Kanchanara Guggulu, Jeevarakshak, Punarnava Mandura, etc.

The dosage of the formulations that are used in the various embodiments of the method herein may vary depending on the patients' requirement. The dosage of the herbal formulation if in tablet form may vary from 125 mg to 1.5 grams per dose, if in liquid form may vary from 15 to 20 ml per dose, and if in powder form may vary from 3 to 5 gram per dose. The dosage of the target specific formulation may vary depending on the patient, In an embodiment, the dosage of the target specific formulation may from 500 mg to 1 gram per dose. The dosage of the bioactive formulation may vary from 2 to 4 drops per day. In an embodiment, the bioactive drops are administered before food, preferably an hour before breakfast. In an embodiment, the herbal formulation and the target specific formulation may preferably be administered after food.

Detoxification Therapies

The detoxification therapies disclosed in the various embodiments herein may include any procedure known to detoxify human body. In an embodiment, the detoxification therapies are procedures of Ayurveda known to detoxify human body. In an embodiment, the detoxification therapy is a combination of Panchakarma therapies. In another embodiment, detoxification therapies include Takra Dhara and Taila Dhara like procedures which are known to reduce stress and bring about normal sleep pattern. In an embodiment, the detoxification therapies include procedures like Ayurvedic Basti with selected drug combination used to regularize bowel habits, improve appetite, reduce pain and bring about lightness in the body.

Further, the detoxification therapies may further include intake of anti-oxidant supplements. The anti-oxidant supplements may be any generally known anti-oxidant supplements. In an embodiment, the anti-oxidant supplements are ayurvedic supplements having herbs, spices and vegetables having anti-oxidant, anticancer and immune modulating properties. In an embodiment, anti-oxidant supplements are ones that include Vitamin C, Vitamin E, alkaloids, bioflavonoids, etc. which are known to detoxify the body.

Diet

Specific diet disclosed in the various embodiments herein may include any healthy diet generally known for cancer patients. In an embodiment, the specific diet is one including rich sources of anti-oxidants. In an embodiment, the rich sources of antioxidant may be fruits and vegetables. In an embodiment, the specific diet includes higher intake of fruits and vegetables. The specific diet plan may vary depending on the patients' condition. For example, a patient having breast cancer may be maintained on a high fruits and vegetables intake to facilitate high plasma carotenoid concentration.

Lifestyle

Maintaining a healthy lifestyle as disclosed in the various embodiments herein may include following any day-to-day regimen suitable for a cancer patient. In an embodiment, maintaining healthy lifestyle includes following daily regimens (Dinacarya) and seasonal regimen (Ritucarya). Dinacarya and Ritucarya provide healthy lifestyles as per the textual descriptions in Ayurveda. In an embodiment, the healthy lifestyle may be maintained depending on one's constitution, season etc.

Meditation

Meditation disclosed in the various embodiments herein may include any generally known form of meditation. In an embodiment, meditation is performed such that it helps awaken patient's cellular intelligence, improves psychological functioning, reduces stress symptoms, enhances coping and well-being, and even overcome the fear of death which facilitates in prolonging patient's life span. In an embodiment, meditation includes Samatha, Anapana Sati, Maitri Dhyana, Pranayama, etc. In another embodiment, meditation includes maintaininga patient's mind in present tense. The duration of meditation may be varied to suit the patient. In an embodiment, a patient may meditate anywhere between 10 to 45 minutes per day.

In an embodiment, meditation may be performed according to the teachings of Buddha. In another embodiment, meditation includes performing Anapanasati. For example, in Anapanasati, one (patient) is required to sit straight with spinal cord in erect position using Padmasana. Thereafter, one is required to observe his own normal breathing by keeping/concentrating his mind near the tip of the nose or near abdomen. As soon as one starts observing his/her own breathing one starts getting umpteen number of thoughts. Then instead of observing the breathing one should start observing the thoughts. By that time one realizes that there are only five types of thoughts one can get while meditating. And for that matter all human beings get only five types of thoughts. One's meditation never starts until these thoughts are prevented. For this Buddha has preached the Arakkha Bhaavana or Rakshana Manthra which are the preventing measures to keep away all the five obstacles. Buddhanussati prevents the thoughts connected with restlessness, laziness and doubts. Mettaanussati prevents the thoughts connected with anger. Asubaanussati and Maranaanussati prevents the thoughts connected with sense organs. Once all the obstacles are removed/prevented real meditation starts and one gets different absorptions (Zaana) and finally gets Enlightenment (Nibban)

Pyramid Therapy

The pyramid therapy disclosed in the various embodiments herein includes performing meditation activities within Pyramids constructed with specific angles and dimensions. In an embodiment, the therapy is performed by meditating in pyramids made up of wooden parts (such as teakwood) with precise dimensions.

In an embodiment, the pyramids are constructed in such a way so as to facilitate the prevention of tissue degeneration and assist tissue regeneration. For example, the space within the great pyramid and its smaller replicas is believed to have an anti-stress effect. Research has shown that the energy field within the pyramid can protect the hippocampal neurons of mice from stress-induced atrophy and also reduce neuroendocrine stress, oxidative stress and increase antioxidant defense in rats (Bhat M S, Rao G, Murthy K D, Bhat P G (2007). Housing in Pyramid Counteracts Neuroendocrine and Oxidative Stress Caused by Chronic Restraint in Rats. *Evidence-based Complementary and Alternative Medicine.* 2007; 4(1):35-42. doi:10.1093/ecam/ne1049). The results showed that housing in pyramid counteracts neuroendocrine and oxidative stress caused by chronic restraint in rats.

The invention is further described by reference to the following examples by way of illustration only and should not be construed to limit the scope of the present invention. It will be apparent to those skilled in the art that many modifications, both to materials and methods, may be practiced without departing from the scope of the present invention.

EXAMPLE 1

A patient having swelling in the anterior aspect of neck and no apparent constitutional symptoms was administered with the Test drug. The patient was suspected of having Papillary Carcinoma.

Cytological diagnosis revealed Hashimoto's thyroiditis with occasional papilary clusters. The swelling was firm, nodular and moving up during deglutition. No lymph nodes involved.

Blood Pressure: 150/100 mmHg.
Thyroid profile: T3: 112 ng/dL (normal range: 60-200)
T4: 2.6 µg/dL (normal range: 4.5-12.0)
TSH: 97.48 µIU/mL (normal range: 0.30-5.5)

It was observed that the swelling had markedly reduced in 45 days course of administration.

Blood Pressure: 140/86 mmHg.
Thyroid profile: T3: 101 ng/dL (normal range: 60-200)
T4: 6.3 µg/dL (normal range: 4.5-12.0)
TSH: 20.34 µIU/mL (normal range: 0.30-5.5)

The patient was administered with an embodiment of the disclosed formulation and observed for improvement. The TSH level improved and dropped to 5.2 µIU/mL with no clinical features.

EXAMPLE 2

A patient having carcinoma of sigmoid colon, post-operative, post chemotherapy with the metastasis at Liver and Lungs and complaints of loss of appetite, gaseous distension of abdomen and mild cough was administered with the test drug at a dose of two 500 mg tablets twice daily. Patient was under constant observation. In due course, the patient exhibited substantial improvement in condition.

Table 2 depicts the results of the Liver function test (LFT). It was observed that the SGOT (Serum glutamic oxaloacetic transaminase) and SGPT (Serum glutamate pyruvate transaminase) levels which were elevated had significantly reduced with increase in appetite and reduction in gaseous distension of abdomen.

TABLE 2

| LFT data | | |
|---|---|---|
| Parameters | Before treatment | After treatment |
| Serum bilirubin: | | |
| Total | 0.83 mg/dl | 0.72 mg/dl |
| Direct | 0.3 mg/dl | 0.2 mg/dl |
| Indirect | 0.62 mg/dl | 0.52 mg/dl |
| Total protein | 6.6 mg/dl | 6.8 mg/dl |
| Albumin | 4.2 mg/dl | 4.4 mg/dl |
| Globulin | 2.4 mg/dl | 2.4 mg/dl |
| A:G Ratio | 1.75 mg/dl | 1.8 mg/dl |
| SGOT | 61.0 IU/L | 31.0 IU/L |
| SGPT | 74.0 IU/L | 24.0 IU/L |
| Alkaline Phosphatase | 201.0 IU/L | 96.0 IU/L |

EXAMPLE 3

A case of papillary carcinoma of thyroid, with a swelling in the anterior part of neck was administered with the Test drug. The patient was also a diagnosed case of Left Ventricular Hypertrophy and renal failure with complaints of general debility, loss of appetite, pedal oedema and exertional dyspnea.

The test drug was administered periodically with regular follow up. Eventually, the patient showed improvement in all symptoms, and swelling of neck had reduced. Blood urea had reduced from 87 mg to 49 mg, serum creatinine improved from 2.1 to 1.8.

Thyroid Stimulating hormone reduced from 46.5 to 14.53 (normal: 0.3-5.5) which eventually got normalized (4.8 IU/ml).

In due course, this patient showed no symptoms of thyroid cancer and swelling in the neck was completely relieved.

EXAMPLE 4

A patient with infiltrating ductal carcinoma of right breast, post-operative but without any chemotherapy or radiation was administered with the Test drug.

In due course, improvements in general condition like weight, appetite and hemoglobin was observed with no signs of metastasis. Table 3 depicts the changes in Hemoglobin level.

TABLE 3

| Hemoglobin levels before and after treatment. | | |
|---|---|---|
| Parameters | Before treatment | After treatment |
| Hemoglobin | 8.9 gm % | 12.7 gm % |

EXAMPLE 5

A patient with bronchogenic carcinoma of the upper lobe of left lung having complaints of severe cough and breathlessness was administered with the Test drug for over a period. It was observed that the cough had reduced significantly with no signs of metastasis. Eventually, no serious episodes of symptoms were observed but with dramatic remission in respiratory symptoms. CT scan done indicated no signs of bronchogenic carcinoma.

Details:

The CT scan conducted before treatment showed pleural effusion and a lesion measuring about 4 cm in right upper lobe of lungs. After the treatment CT scan showed improvement. No cancer lesions were seen. Only emphysematous changes and fibrosis were noted.

EXAMPLE 6

A patient with carcinoma of lung with severe adverse reactions of chemotherapy like weakness, vomiting, and oral ulcers was administered with the Test drug. The lesion was found to be chemo-resistant. Over a period, the symptoms like cough and breathlessness were considerably reduced; adverse effects of chemotherapy also subsided with no signs of metastasis.

Details:

Irregular lesion measuring about 4 cm in right middle lung near hilum, with mediastinal lymph node enlargement largest about 2 cm, pleural effusion on right side were observed.

EXAMPLE 7

A case of carcinoma of oesophagus and hard palate having complaints of dysphagia, loss of appetite, loss of taste, general debility, and cough with whitish sputum was administered with the Test drug. In due course, the cough was substantially reduced, appetite improved and taste sensation was observed to be slightly better. USG of abdomen did not show any signs of metastasis. Follow up endoscopy indicated no signs of carcinoma.

Details:

Upper GI endoscopy done before treatment showed an ulceroproliferative growth in oesophagus 11 cm from jaw level extending upto about 6.5 cm with narrowing lumen.

Endoscopy done post treatment showed no ulceroproliferative growth, mild fibrosis and slightly narrowed lumen was seen.

EXAMPLE 8

A case of bronchogenic carcinoma (post-operative and chemoresistant) having complaints of cough with haemoptysis, dyspnea and general debility was administered with the Test drug for over a period of time. The patient was also a known case of Type II Diabetes mellitus. In due course, it was observed that the complaints like haemoptysis, cough anddyspnea were drastically reduced.

Eventually, the patient was also observed to have become asymptomatic.

Details:

CT scan of lungs indicated no signs of carcinoma. Report of CT scan of lungs at the time of diagnosis showed a lesion of about 2.5×3 cm extending to hilum in right upper lobe of lungs with a few of hilar lymph nodes enlarged. Post treatment no lesions were observed, fibrous band with calcification was observed.

EXAMPLE 9

A known case of adenocarcinoma of endometrium (post hysterectomy and post chemotherapy) with a history of recurrence as omental deposits was under the administration of the Test drug for a period of time. The patient was also a known case of diabetes mellitus type II and deep vein thrombosis having anemia, dyspnea on exertion, bilateral pedal edema, fullness and pain in abdomen. Abdomen USG were observed to be within normal limits, cancer markers CA-125 and CEA were also found to be with in normal limits. After continuous administration and observation over a period of time, symptoms like paedaloedema and dyspnea had subsided, fullness and abdomen pain had been relieved.

Details:

Before treatment multiple peritoneal (omental deposits) with gross ascites were noted. After treatment no intra abdominal lesions were seen, no free fluid in abdomen and no organomegaly was observed. Over a period of time, CA-125 and CEA levels which initially were around 55.00 U/ml and 18.3 ng/mL, respectively, were reduced.

EXAMPLE 10

A patient with h/o progressive swelling in right side of neck with pain, h/o weight loss, diagnosed to be the secondary of primary lesion at hypopharynx and suggested for neck dissection was under the administration of the Test drug. In due course, neck swelling had reduced, pain has subsided and general condition had stabilized. Also, serum LDH and CEA were observed to be within normal limits after treatment. Table 4 depicts the improvement in serum LDH and CEA levels before and after treatment.

TABLE 4

| Serum LDH and CEA | | |
|---|---|---|
| Marker | Before treatment | After treatment |
| LDH | 1085 U/L | 296 U/L |
| CEA | 10.2 ng/mL | 1.5 ng/mL |

EXAMPLE 11

A known case of adenocarcinoma of rectum post-operative and post chemo therapeutic status having h/o blood mixed stools, loss of appetite, progressive weight loss and general weakness was administered with the Test drug.

In due course, the patient has become asymptomatic with normal CA-125 and CEA levels. Follow up CT scan and USG reports were observed to be within normal limits after treatment.

Details:

Follow up CT scan report did not show any intra abdominal lesion (However patient came after surgery, his first CT scan showed a lesion of about 3.5×4.5 cm in rectum with para coeliac lymph nodes enlarged)

USG report was normal without any intra abdominal lesion, free fluid or organomegaly indicating no metastasis or new lesion Table 5 depicts the improvement in CA-125 and CEA levels before treatment (BT) and after treatment (AT). Weight improved by 4 kgs.

TABLE 5

| CA-125 and CEA levels | | |
|---|---|---|
| Marker | BT | AT |
| CA-125 | 155.0 U/ml | 26.6 U/ml |
| CEA | 22.0 ng/ml | 3.3 ng/ml |

EXAMPLE 12

A Non-Hodgkin's lymphoma patient, high grade large cell type with the h/o incomplete chemotherapy having symptoms of lymphadenopathy of left axillary and inguinal area, general debility and anemia was administered with the Test drug. The patient eventually has been observed to be asymptomatic.

Details:

CT scan taken before treatment showed multiple bilateral inguinal and cervical lymph node enlargement, and follow up CT scan showed no lymphadenopathy Follow up USG abdomen report shows no abnormality. No intraabdominal lymphadenopathy orgnomegaly or free fluid Biopsy report: Sections from the five lymph nodes received show normal architecture. The sections studied from the above lymph nodes do not show histological evidence of lymphoma. Table 6 depicts the LDH levels before and after treatment.

TABLE 6

LDH report

| Parameters | Before treatment | After treatment |
|---|---|---|
| LDH | 630 U/L | 238 L |

Table 7 depicts the change in Hb % after treatment.

TABLE 7

Hb % report

| Parameters | Before treatment | After treatment |
|---|---|---|
| Haemoglobin | 8.0 gm % | 13.8 gm % |

Table 8 depicts the results of LFT after treatment.

TABLE 8

LFT report.

| Parameters | | |
|---|---|---|
| Serum Bilirubin | | |
| Total | 0.73 | mg/dl |
| Direct | 0.3 | mg/dl |
| Indirect | 0.42 | mg/dl |
| Total protein | 7.1 | mg/dl |
| Albumin | 4.6 | mg/dl |
| Globulin | 2.5 | mg/dl |
| A:G Ratio | 1.84 | mg/dl |
| SGOT | 21.0 | IU/L |
| SGPT | 14.0 | IU/L |
| Alkaline Phosphatase | 98 | IU/L |

Table 9 depicts the results of RFT after treatment.

TABLE 9

RFT report.

| Parameters | | |
|---|---|---|
| Serum creatinine | 1.1 | mg/dl |
| Blood Urea | 38 | mg/dl |
| Uric Acid | 5.4 | mg/dl |

EXAMPLE 13

A patient with the h/o colon cancer, post-operative having complaints of bloating of abdomen, urge to defecate after food and marginally elevated CEA levels, was administered with the Test drug for over a period.

Eventually, the patient was observed to become asymptomatic having CEA within normal limits. Table 10 depicts the CEA levels before and after treatment

TABLE 10

CEA details before and after treatment.

| Parameters | Before treatment | After treatment |
|---|---|---|
| CEA | 102.0 ng/mL | 1.3 ng/mL |

EXAMPLE 14

A diagnosed case of chronic myeloid leukemia having symptoms of pain in low back, thighs, intermittent fever and pain abdomen was administered with the Test drug for over a prolonged period. The patient was observed to become asymptomatic with WBC counts and morphology within normal limits. The result of Peripheral smear and BCR-ABL gene study confirmed the diagnosis and is provided hereunder. Table 11 depicts the results of Peripheral smear report before and after treatment.

TABLE 11

Peripheral smear report before and after treatment

| Blood components | Before treatment | After treatment |
|---|---|---|
| RBCs | Normocytic, norochromic, mild anicocytosis | Normocytic, norochromic, no anicocytosis |
| WBC | Markedly increased in number | Normal in number |
| Neutrophils | 43% | 63% |
| Lymphocytes | 02% | 32% |
| Monocytes | 01% | 01% |
| Basophils | 03% | 03% |
| Eosinophils | 0% | 01% |
| Premyelocytes | 03% | Absent |
| Myelocytes | 20% | Absent |
| Bands and Metamyelocytes | 28% | Absent |
| Blasts | Occasional | Absent |
| Platelets: | Adequate (giant forms) | Adequate (normal forms) |

Peripheral smear report showing WBC counts and morphology within normal limits are as follows: RBCs: Normocytic normochromic; WBCs: Within normal limits; Neutrophils: 62%; Lymphocytes: 32%; Monocytes: 01%; Basophils: 01%; Eosinophils: 04%.

Before treatment: The hybrid transcript for BCR-ABL was detected in the leukocytes of the specimen (Genomic breakpoint observed: e13a2 corresponding to p210).

BCR-ABL gene rearrangement (PCR-Quantitative):

ABL rearrangement: 0.2

Type of translocation: M-BCR

After Treatment:

BCR-ABL/ABL transcript: Transcript not in detectable limits

Table 12 depicts the Total Leukocytes before and after treatment:

TABLE 12

Total Leukocytes before and after treatment:

| Before treatment | After treatment |
|---|---|
| 33000 cells/micro liter | 7600 cells/micro liter |

EXAMPLE 15

A case of borderline mucinous tumor of right ovary hysterectomy was administered with the Test drug. Over a period, the general condition had improved. It was also observed that symptoms like abdominal distension and discomfort were completely relieved.

The patient was observed to become asymptomatic with normal levels of cancer markers and USG study.

Details:

USG report showed: Patient had a large tumor in right ovary (5.6×7.2 cm) with moderate ascites as was seen in her USG abdomen pelvis before treatment. Post-operative and after our treatment when USG was repeated no lesions, no free fluid, no organomegaly was observed, uterus was not visible as it was post hysterectomy status. Table 13 depicts the change in CA-125 and CA 19-9 levels.

TABLE 13

Cancer marker levels before and after treatment.

| Markers | Before treatment | After treatment |
|---|---|---|
| CA-125 | 65.00 U/ml | 14 U/ml |
| CA 19-9 | 68 U/ml | 18 U/ml |

EXAMPLE 16

A known case of adenocarcinoma of colon with post-operative status, but without any chemotherapy had been administered with the Test drug for over a certain period.

Eventually, the patient was observed to become asymptomatic with no radiological, haematological or biochemical abnormalities.

Details:

X ray findings were as follows: No pleural effusion, no lesions, hilar lymph nodes normal, essentially a normal chest X ray was observed.

Haematological and biochemical results were as follows: Hb %: 14.2 gm %; RBCs: 5 million/cmm; WBCs: 7.8×109 L; Neutrophils: 64%; Lymphocytes: 32%; Monocytes: 0%; Basophils: 01%; Eosinophils: 03%.

EXAMPLE 17

A diagnosed case of chronic lymphocytic leukemia having symptoms of intermittent fever, exhaustion, exertional dyspnea, multiple lymphadenopathy (especially axillary and cervical) was administered with the Test drug, without any allopathic intervention.

Eventually, it was observed that the lymphadenopathy had markedly reduced, fever relieved and LDH level had improved. Table 14 depicts the change in LDH levels after treatment.

TABLE 14

LDH levels before and after treatment.

| Parameter | Before treatment | After treatment |
|---|---|---|
| LDH | 656 U/L | 286 U/L |

The patient was observed to be comfortable except for a few episodes of dyspnea (the patient is a known case of bronchial asthma, diabetes mellitus and hypertension).

EXAMPLE 18

A known case of recurrent fibro sarcoma, post-operative and incomplete chemotherapy status having swelling in right thigh, intermittent fever, and blood mixed stools and general debility was administered with the Test drug for over a period. Eventually, all symptoms were observed to have subsided except for edema in right lower limb. Further investigations showed no signs of recurrence.

EXAMPLE 19

A known case of ovarian carcinoma with hepatic metastasis having features of tense ascites, general debility, and loss of appetite and pain in abdomen was administered with the Test drug. Over a period of time, ascites were observed to have been completely relieved, appetite improved and pain reduced. USG done after treatment showed no lesions in abdomen or pelvis, liver was normal and no free fluid in abdomen.

Details:

Follow up USG study of abdomen and CA-125 level were also observed to be normal. USG report before treatment showed a lesion measuring 3.2×4.6 cm in right ovary with multiple lesions in right lobe of liver, largest measuring 2.8 cm and gross ascites. Table 15 depicts the change in CA 125 levels after treatment.

TABLE 15

CA 125 levels before and after treatment.

| Markers | Before treatment | After treatment |
|---|---|---|
| CA-125 | 665.00 U/ml | 34 U/ml |

EXAMPLE 20

A known case of adenocarcinoma of pancreas (unresectable) having complaints of distension and pain in abdomen was under the administration of the Test drug. Patient's follow up CT scan reports, during the course, indicated reduction in tumor mass. Patient was observed to have become asymptomatic.

Details:

CT scan report showed Moderate size (9.7×5.8×7.1 cm) lobulated hypoechoic soft tissue mass lesion in preaortic region. Over a period of time post treatment, the size of the lesion got reduced to 6.0×5.7 cm in head of pancreas with few areas of calcification.

EXAMPLE 21

A diagnosed case of small cell carcinoma of cervix having complaints of watery and occasional blood tinged discharge per vagina and pain in lower abdomen was administered with the Test drug. In due course, the patient's PV examination was observed to be normal having healthy cervix without any discharge or touch bleed. Also, USG abdomen pelvis showed no abnormalities.

Details:

Per vaginal examination findings were as follows:
1. Labia minora, majora and clitoris: No lesions, scars, tears observed.
2. Inspection and palpation of vulva: The introitus—No discharge or bleeding, no ulcers, vaginal mucosa pinkish, no prolapse observed
3. Speculum examination: the labia are separated with the index finger and thumb of left hand. The lubricated closed speculum (correct size) is inserted through the introitus into the vaginal canal without any rotation i.e. closed blades are horizontal with speculum handles pointing posteriorly in the lithotomy position or anteriorly if using the examination couch. Cervix: Healthy with fibrosis (healed lesion), no touch bleed, slight serous discharge.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. A method of treatment and management of Cancer, said method comprising: administering to a patient in need thereof a therapeutically effective amount of a herbo-mineral formulation and a bioactive formulation, wherein said herbo-mineral formulation comprises
   *Withania somnifera* in an amount in the range of 6 to 10 wt. %,
   *Sida cordifolia* in an amount in the range of 6 to 10 wt. %,
   *Asparagus racemosus* in an amount in the range of 4 to 8 wt. %,
   *Tinospora cordifolia* in an amount in the range of 4 to 8 wt. %,
   *Moringa oleifera* in an amount in the range of 4 to 8 wt. %,
   *Picrorhiza kurroa* in an amount in the range of 4 to 8 wt. %,
   *Ocimum sanctum* in an amount in the range of 6 to 8 wt. %,
   *Curcuma longa* in an amount in the range of 5 to 9 wt. %,
   shilajit in an amount in the range of 4 to 8 wt. %,
   Abhraka Bhasma in an amount in the range of 2 to 4 wt. %,
   Trivanga Bhasma in an amount in the range of 0 to 2 wt. %,
   Pravala Bhasma in an amount in the range of 0 to 2 wt. %,
   Loha Bhasma in an amount in the range of 2 to 4 wt. % and
   Swarna Makshika Bhasma in an amount in the range of 0 to 2 wt. %, of the total composition; and
   said bioactive formulation comprises of processed Swarna bhasma and medicated honey.

2. The method of treatment and management of Cancer as claimed in claim 1, wherein said herbo-mineral formulation further comprises of at least one herb selected from the group consisting of *Terminalia chebula, Terminalia bellerica, Emblica officinalis, Piper longum, Piper nigrum* and *Zingiber officinalis*.

3. The method of treatment and management of Cancer as claimed in claim 1, further comprising administrating to the patient a therapeutically effective amount of at least one target specific formulation.

4. The method of treatment and management of Cancer as claimed in claim 3, wherein said target specific formulation is selected from the group consisting of Kanchanara Guggulu, Jeevarakshak and Punarnava Mandura.

5. The method of treatment and management of Cancer as claimed in claim 3, wherein said target specific formulation is selected from the group consisting of purine ring inhibitors, ribonucleotide reductase inhibitors, dTMP synthesis inhibitors, DNA synthesis inhibitors, DNA intercalators, protein synthesis inhibitors and microtubule function inhibitors.

6. The method of treatment and management of Cancer as claimed in claim 1, wherein said herbo-mineral formulation is administered in solid form in a therapeutically effective amount in the range of 125 mg to 1.5 grams per dose.

7. The method of treatment and management of Cancer as claimed in claim 1, wherein said bioactive formulation is administered in the form of drops in a therapeutically effective amount in the range of 2 to 4 drops per day.

8. The method as claimed in claim 4, wherein said target specific formulation is administered in an amount in the range of 500 mg to 1 gram per dose.

9. The method of treatment and management of cancer as claimed in claim 1, wherein said cancer is at least one condition selected from the group consisting of carcinoma of oesophagus, carcinoma of lung, bronchogenic carcinoma, adenocarcinoma of endometrium, adenocarcinoma of rectum, Non-Hodgkin's lymphoma, Dalton Cell lymphoma, chronic myeloid leukemia, borderline mucinous tumor, adenocarcinoma of colon, fibro sarcoma, ovarian carcinoma, Cervix Adenocarcinoma and carcinoma of pancreas.

10. The method of treatment and management of cancer as claimed in claim 1, wherein said cancer is Dalton Cell lymphoma.

11. The method of treatment and management of Cancer as claimed in claim 1, further comprising detoxification therapy, diet management, healthy lifestyle, meditation and pyramid therapy.

12. The method of treatment and management of Cancer as claimed in claim 11, wherein said detoxification therapy comprises Panchakarma therapy, Takra Dhara, Taila Dhara and Ayurvedic Basti.

13. The method of treatment and management of Cancer as claimed in claim 11, wherein said diet management comprises maintaining anti-oxidant rich diet.

14. The method of treatment and management of Cancer as claimed in claim 11, wherein said healthy lifestyle comprises maintaining at least one regimen selected from the group consisting of Dinacarya and Ritucarya.

15. The method of treatment and management of Cancer as claimed in claim 1, wherein said herbo-mineral formulation is administered in liquid form in a therapeutically effective amount in the range of 15 to 20 ml per dose.

16. The method of treatment and management of Cancer as claimed in claim 1, wherein said herbo-mineral formulation is administered in powder form in a therapeutically effective amount in the range of 3 to 5 gram per dose.

* * * * *